US009814458B2

(12) United States Patent
North (10) Patent No.: US 9,814,458 B2
(45) Date of Patent: Nov. 14, 2017

(54) APPARATUS AND METHOD FOR IMPLANTING AND SECURING THE POSITION OF IMPLANTABLE MEDICAL DEVICE

(71) Applicant: Richard B. North, Baltimore, MD (US)

(72) Inventor: Richard B. North, Baltimore, MD (US)

( * ) Notice: Subject to any disclaimer, the term of this patent is extended or adjusted under 35 U.S.C. 154(b) by 233 days.

(21) Appl. No.: 14/715,973

(22) Filed: May 19, 2015

(65) Prior Publication Data

US 2015/0257755 A1 Sep. 17, 2015

Related U.S. Application Data

(62) Division of application No. 13/640,610, filed as application No. PCT/US2011/021239 on Jan. 14, 2011, now Pat. No. 9,034,000.

(60) Provisional application No. 61/336,098, filed on Jan. 15, 2010.

(51) Int. Cl.
| | |
|---|---|
| A61B 17/04 | (2006.01) |
| A61N 1/375 | (2006.01) |
| A61M 25/02 | (2006.01) |
| A61M 5/142 | (2006.01) |
| A61M 39/02 | (2006.01) |
| A61B 17/06 | (2006.01) |
| A61N 1/05 | (2006.01) |

(52) U.S. Cl.
CPC ...... *A61B 17/0482* (2013.01); *A61B 17/0485* (2013.01); *A61M 25/02* (2013.01); *A61N 1/375* (2013.01); *A61B 17/0469* (2013.01); *A61B 17/06066* (2013.01); *A61B 2017/0496* (2013.01); *A61M 5/14276* (2013.01); *A61M 2025/0286* (2013.01); *A61M 2039/0223* (2013.01); *A61N 1/05* (2013.01); *A61N 1/3752* (2013.01)

(58) Field of Classification Search
CPC . A61B 17/04; A61B 17/0482; A61B 17/0469; A61B 17/06066; A61B 2017/0496; A61B 2017/00663; A61M 25/02
See application file for complete search history.

(56) References Cited

U.S. PATENT DOCUMENTS 6,352,542 B1 * 3/2002 Snyder ............... A61B 17/0482
606/148
2002/0045908 A1 * 4/2002 Nobles ............... A61B 17/0057
606/144

* cited by examiner

*Primary Examiner* — Victor Nguyen
(74) *Attorney, Agent, or Firm* — Whiteford, Taylor & Preston, LLP; Gregory M. Stone (57) ABSTRACT

Disclosed is an apparatus and method for facilitating the implantation and secure positioning of implantable medical devices within a subcutaneous pocket formed by a surgeon within the patient. Such apparatus and method are configured to address the above-described challenges of containing implantable medical devices within such subcutaneous pockets, and the spring-like leads or catheters that may be attached to them, during implantation.

9 Claims, 9 Drawing Sheets

APPARATUS AND METHOD FOR IMPLANTING AND SECURING THE POSITION OF IMPLANTABLE MEDICAL DEVICE

CROSS REFERENCE TO RELATED APPLICATION

This application is a divisional of U.S. patent application Ser. No. 13/640,610 entitled "Apparatus And Method For Implanting And Securing The Position Of Implantable Medical Device," filed with the U.S. Patent and Trademark Office on Oct. 11, 2012 (now U.S. Pat. No. 9,034,000 issued May 19, 2015), which application is a national stage entry under 35 U.S.C §371 of International Patent Application No. PCT/US2011/021239 filed Jan. 14, 2011, which application is based upon and claims the benefit of U.S. Provisional Patent Application Ser. No. 61/336,098 filed Jan. 15, 2010, the specifications of which are incorporated herein by reference in their entireties.

TECHNICAL FIELD

The present invention relates generally to the field of medical devices, and particularly to an apparatus and method of using the same that facilitate implantation and secure positioning of implantable medical devices in a subcutaneous pocket.

BACKGROUND ART

Medical devices such as pacemakers, stimulators or drug delivery systems are typically implanted subcutaneously; this minimizes the invasiveness of the procedure and facilitates access, whether by electrical coupling (e.g. for charging or telemetry) or physically (e.g. needle access). Implantation may be rather like stowing a Jack-in-the-box, in that during and even after implantation, the medical device may at any moment pop out of the subcutaneous pocket in which it is implanted. Such devices commonly have leads or catheters coiled behind or beneath them, like the spring in such a Jack-in-the-box toy.

A related problem is that following implantation, the device may flip over. Even after encasement in an envelope of fibrous scar tissue, unless it is constrained it retains this potential. If it is a pump with a refill port on one side, or an electronic implant with a charging or telemetry coil on one side, this can render it nonfunctional. If it flips over repeatedly, it may twist the lead or catheter to the point that it kinks, breaks, pulls out at its distal end, or otherwise fails.

FIGS. 1-7 (PRIOR ART) show a typical implant 10. Implantable medical devices, such as by way of non-limiting example electrical stimulation devices, which typically have multicontact leads attached, accordingly have a plastic header/connector assembly 12 as shown in the Figures; implanted drug delivery systems and pumps, which typically have simple catheter connections, may not have a separate header. Plastic headers and housings typically have one or more holes 14 drilled through them, and metal "can" enclosures may have metal suture loops attached. These holes and loops accept sutures, which are placed through tissue around the implant and then tied, holding the implant in position.

Figure 1:
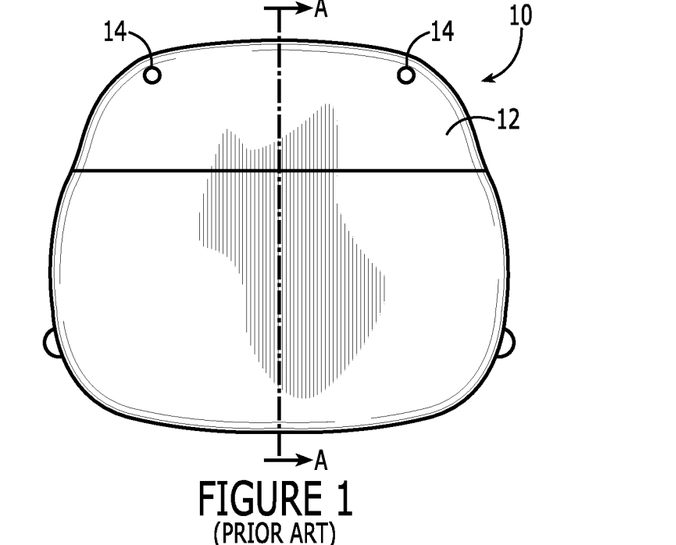
FIG. 1 is an illustration of a prior art implantable medical device including suture holes and loops.
Figure 2:
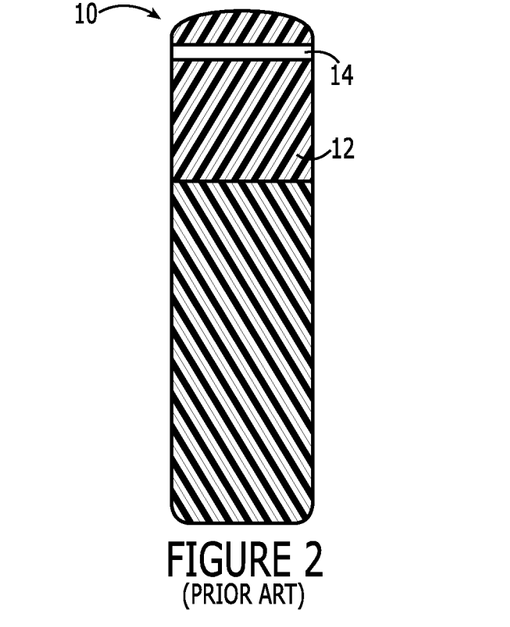
FIG. 2 is a sideview, cut-away illustration of the implantable medical device of FIG. 1.
Figure 3:
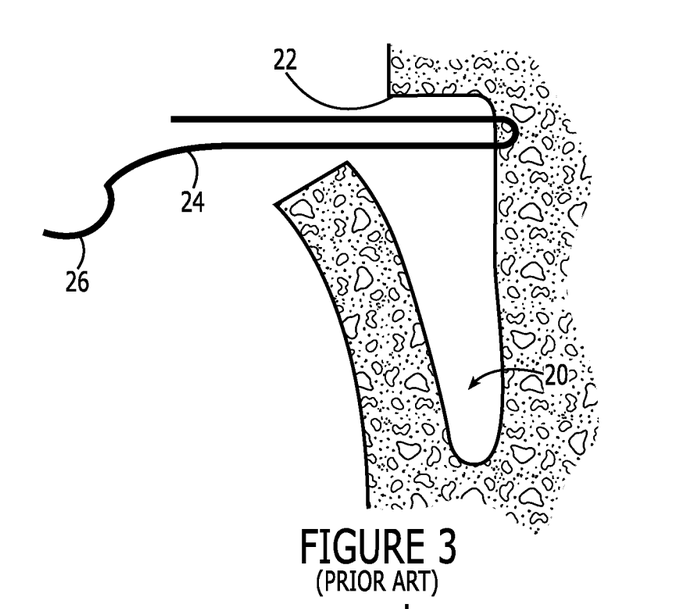
FIG. 3 is an illustration of a subcutaneous pocket within which an implantable medical device may be implanted and illustrating the engagement of a suture with the skin or tissue within the pocket.

FIG. 3 shows a side, cross-section view of a typical subcutaneous pocket formed during surgical implantation. The pocket 20 is typically created on one side, and not both sides, of the surgical incision 22. Thus when the incision is closed, typically by suturing with a suture 24 and needle 26, the wound closure is not directly over the implanted device. This avoids pressure from the device directly on the healing wound, which might cause it to break down; and it increases the path length from the device to the surface, reducing the risk of drainage from or egresss through the wound or ingress of contamination from the outside. The thickness of tissue alongside, rather than over the device, facilitates a secure closure in multiple layers.

Figure 4:
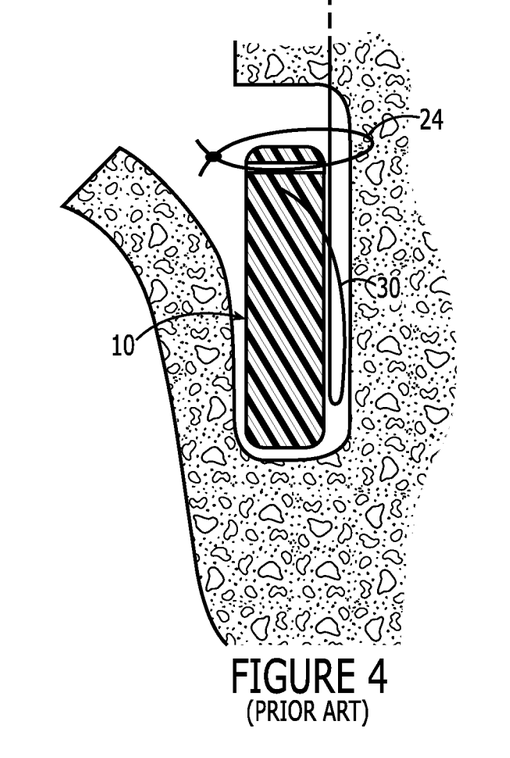
FIG. 4 is an illustration of the subcutaneous pocket including an implantable medical device positioned therein and further illustrating the use of a suture to secure the device within the pocket and a lead wire looped behind the device and extending therefrom.

FIG. 4 shows the common current practice of coiling redundant loops of lead or catheter 30 behind the implant 10, and then suturing the header to subcutaneous tissues. This serves the dual purpose of containing the coils and securing the implant, so that (1) during closure the coils are out of the way, and (2) after closure the implant remains secure against movement, including extrusion through the wound as well as flipping over, with coils behind it. To the extent the coils remain mobile, they provide strain relief when traction is applied to the lead by patient movement.

Figure 5:
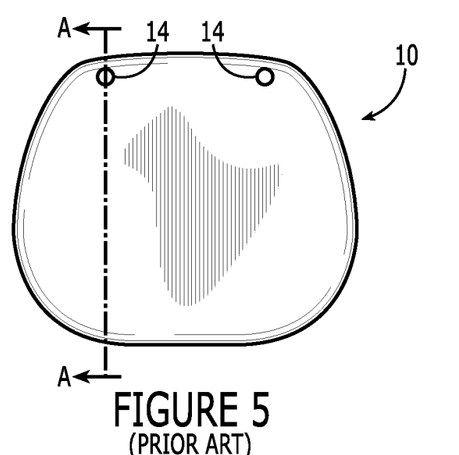
FIG. 5 is an illustration of an implantable medical device including suture holes.
Figure 6:
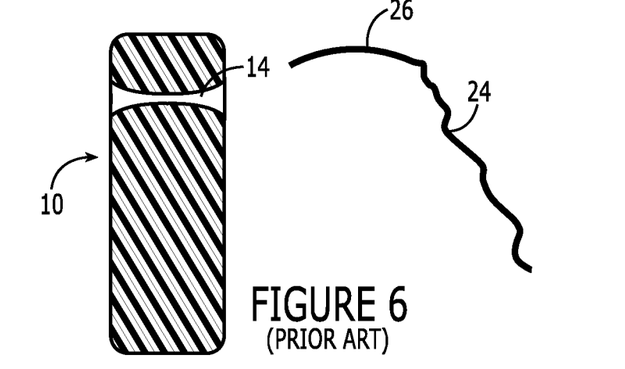
FIG. 6 is a side, cross-sectional view of the implantable medical device of FIG. 5 along section line A-A and comprising a curved suture hole.
Figure 7:
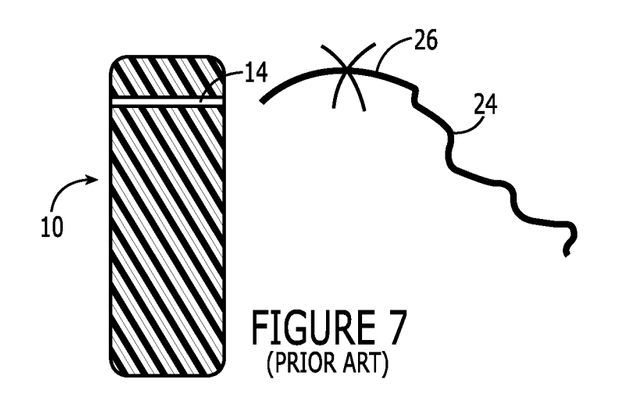
FIG. 7 is a side, cross-sectional view of the implantable medical device of FIG. 5 along section line A-A and comprising a straight-line suture hole.

As shown in FIG. 5-6, radiusing the suture holes 14 to accommodate curved needles 26, with as pronounced a curve and as large a diameter as the surgeon might reasonably choose, facilitates suture placement. (Many current devices have a small straight hole which impedes passage of a curved needle, as shown in FIG. 7.) A silicone rubber plug might fill a larger hole to stabilize the suture during implantation and control tissue ingrowth afterwards.

Asymmetry about the axis of the emerging lead or catheter tends to resist flipping over, once the implant is encapsulated in scar. If the lead or catheter emerges tangentially, the implant is not as free to rotate around it, as it would be if it emerges radially, similar to the stick on a lollipop.

Notwithstanding these prior art configurations, there remains a need in the art to provide for the secure attachment of an implantable medical device within a subcutaneous pocket that may be performed without requiring extraordinary testing on the part of the surgeon.

DISCLOSURE OF INVENTION

Disclosed is an apparatus and method for facilitating the implantation and secure positioning of implantable medical devices within a subcutaneous pocket formed by a surgeon within the patient. Such apparatus and method are configured to address the above-described challenges of containing implantable medical devices within such subcutaneous pockets, and the spring-like leads or catheters that may be attached to them, during implantation.

With regard to certain aspects of a particularly preferred embodiment, the invention comprises an implantable medical device having a housing, at least one channel extending into the housing, and a retaining appliance removably positioned within the channel, the retaining appliance having a connecting arm configured to fit within and remain removably held within the channel, and a retaining arm attached to the connecting arm and extending away from the connecting arm at an angle to the connecting arm.

With regard to further aspects of a particularly preferred embodiment, the invention comprises an implantable medical device having a housing and a plurality of suture engaging members each configured to receive a portion of a suture therein, wherein the suture engaging members are positioned with respect to one another such that tightening a suture that engages both of the suture engaging members and extends through tissue within a patient's body against which the housing is to be implanted will cause the housing to be pulled against such tissue.

Finally, and with regard to yet further aspects of a particular preferred embodiment, the invention comprises a method for securing the position of an implantable medical device, which method includes providing an implantable medical device having a housing and a plurality of suture engaging members each configured to receive a portion of a suture therein, wherein the suture engaging members are positioned with respect to one another such that tightening a suture that engages both of the suture engaging members and extends through tissue within a patient's body against which the housing is to be implanted will cause the housing to be pulled against the tissue; forming a subcutaneous pocket in a patient's body having an interior pocket wall; placing a suture through the back wall of the pocket; removing a sewing needle from the suture so as to provide two free ends of the suture; tying the free ends of the suture to cause the suture to form a tightenable suture loop; inserting portions of the tightenable suture loop into the suture engaging members; and tightening the suture loop so as to draw the implantable medical device into a final implanted position within the pocket.

BRIEF DESCRIPTION OF THE DRAWINGS

The numerous advantages of the present invention may be better understood by those skilled in the art by reference to the accompanying drawings in which.

BEST MODE(S) FOR CARRYING OUT THE INVENTION

The following description is of a particular embodiment of the invention, set out to enable one to practice an implementation thereof, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

The apparatus and method described herein facilitate implantation of a typical pulse generator, pump, or similarly configured implantable medical device, in a subcutaneous pocket, and management of redundant lead or catheter attached to such device. As used herein, the term "catheter" is intended for use in its broadest form so as to encompass hollow tubes configured for carrying materials from an implantable medical device to desired locations in a patient's body, as well as electrical leads or other cables and similar devices configured for connection to and extending outward from an implantable medical device. Certain modifications to the basic, unadorned implant are contemplated (e.g., slots providing access to suture holes) to accommodate variously configured modular attachments that may facilitate implantation, particularly for the less experienced or unassisted operator.

Such apparatus and methods are configured to secure an implant and redundant lead or catheter devices connected to an implant. The implant is typically a subcutaneously implanted medical device such as a pacemaker, stimulator or drug delivery system. In preferred exemplary embodiments of the current invention, the implant includes a header or connector assembly connected with a housing or "can". In alternative embodiments, the implant may be configured in various manners, such as including a single housing or a first and second housing connected with a header or connector assembly. Implants may be preferably constructed of plastic materials, metals, or other such biologically inert materials as may be contemplated by those skilled in the art. It is further contemplated in exemplary embodiments of the current invention that the implant may include a shield or a coating of a biologically inert material that is positioned between the implant and surrounding tissue.

Generally, the header or connector assembly may include various apertures (e.g., suture holes) that provide access to channels that extend at least partially into or through the housing. The suture holes and channels are preferably configured to receive sutures to assist in the secure positioning of the implant. Preferably, the implants have one or more holes and channels through them. In a preferred embodiment, a pair of suture holes, located on opposite ends of a channel, provide the terminus of the channel where it extends through the implant. Optionally, the implant may only contain one channel, or even more than two channels, as may be contemplated by those skilled in the art. It is further contemplated that the channels may be oriented as linear or straight passages or may include various angular orientations with respect to the outer surface of the implant, and may be variously located about the header or connector assembly and/or the can or the implant. For example, the channels may provide a passage for a suture that allows the suture to enter and exit the passage on the same side of the implant or on opposite sides of the implant.

Referring generally now to FIGS. 8A through 12, exemplary embodiments are shown including methods of promoting the secure positioning of an implant or anchoring of the implant. These methods also include the use of novel apparati and/or novel structural features included within the implant.

Figure 8A:
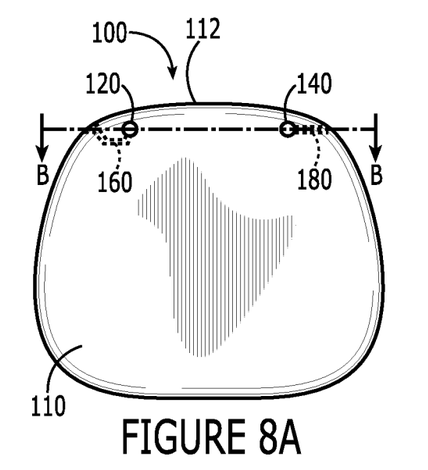
FIG. 8A is an illustration of an implantable medical device including suture energy members in the form of slotted suture holes in accordance certain aspects of an exemplary embodiment of the invention.
Figure 8B:
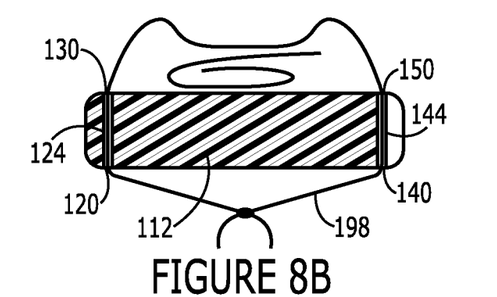
FIG. 8B is a top, cross-sectional view of the implantable medical device of FIG. 8A including a suture engaging the slotted suture holes and further illustrating the suture threaded through tissue and the position of lead coils.

With particular reference to FIGS. 8A and 8B, an implant 100 includes a housing 110 with suture engaging members that include a first suture hole 120 and a second suture hole 140, generally located on opposite sides of the housing and proximal to a top end 112 of the housing. The first and second suture holes are designed to receive sutures or other restraining-type devices that allow a user to secure the position of the implant within a subcutaneous pocket. First suture hole 120 provides a terminus of a first end of a first suture channel 124 that extends through the housing 110. A second suture hole 130 forms the terminus of a second end of the first suture channel 124. Similarly, a third suture hole 140 is the terminus of a first end of a second suture channel 144 that extends through the housing 110. A fourth suture hole 150 forms the terminus of a second end of the second suture channel 144. It is to be understood that the position or location of the termini for the first through fourth suture holes and/or first and second suture channels may vary throughout the housing 110.

As shown in FIG. 8A, also forming a part of such suture engaging members and extending from the first suture hole 120 through the outer edge of the housing 110 is a first slot 160, and from the second suture hole 140 is a second slot 180. The first and second slots provide an aperture that extends from the outer edge of the housing into the first and second channels, respectively. The addition of the first and second slots allows access by a suture from the outside of the housing to the first and second channels. In the current embodiment, the first and second slots extend the length of the first and second channel and allow the suture to seat within the first and second channel.

The first and second slot may allow a single suture to perform the function of two or more. In operation, by way of the example shown in FIG. 8B, the suture may first be placed through the back wall of the pocket, one or two times, and its needle removed and the ends of the suture tagged. The lead wire(s) or catheter(s) may be coiled behind the implant, all may be introduced into the pocket together, and then the suture may be inserted through the slots and seated in the channels and tied, drawing the implant down into final position.

The configuration of the first and second slot may vary to accommodate the receipt and passage of variously sized sutures into the first and second channels. It is contemplated that the configuration of the slot(s) may be varied to promote the exclusion and/or retention of sutures within the channel(s). For instance, the width of the slot(s) may be varied, such as minimized, to exclude sutures above a certain diameter. The slot(s) may be configured in a tapered manner so as to admit sutures but then not allow them to back out. The angular contouring of slots within the implant may promote greater tissue contact and promote an increase in the tangential nature of incident forces acting upon the implant and the suture when in operation. In a preferred embodiment, the contour of the slot might present in a generally linear or straight orientation. In the alternative, the contour of the slot may include one or more different angular orientations, or a more complex contour, as shown for first slot 160, to manage the forces acting on the implant during and after surgery.

By allowing the use of a single suture, the use of these slots not only facilitates implantation, but it also reduces the tendency of separate sutures to cut through tissue, because the area of tissue contact is greater and the incident forces are more tangential. This is important not only during but also after implantation, when the suture(s) remain important to prevent movements, such as flipping over, of the implant.

Figure 9:
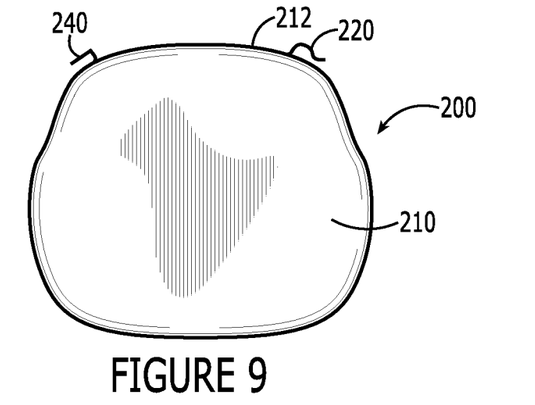
FIG. 9 is an illustration of an implantable medical device including suture engaging members in the form of cleats for connecting a suture with the implantable medical device in accordance with further aspects of an exemplary embodiment of the invention.

Alternatively, the suture engaging member may be provided in the form of a post(s), cleat(s) and/or hook(s), as shown in FIG. 9, connected to a housing 210 of an implant 200 to accomplish a similar function to that of the slots 180. More particularly, a first post, cleat, or hook 220 is shown connected to a top side 212 of the housing 210 and a second post, cleat, or hook 240 is connected opposite the first on the top side 212. The number of these features connected with an implant may vary. The location upon the housing of these features may also vary to accomplish their function.

Figure 10:
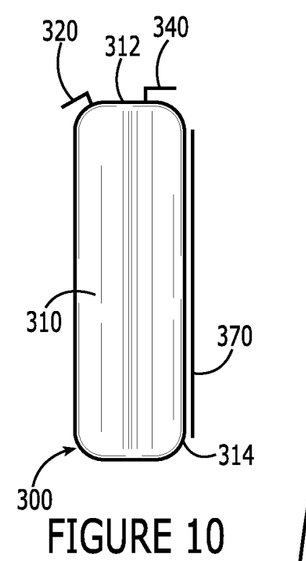
FIG. 10 is a sideview of an implantable medical device with cleats and further including a coating or shield on a back surface of the device.

An implant 300, shown in FIG. 10, includes a first post 320 and second post 340 connected to a top side 312 of a housing 310 of the implant. In operation these two suture engaging members allow a user to secure the position of the implant 300 within a pocket through coupling with one or more sutures and/or other restraining devices. In the current embodiment, implant 300 also includes a coating or shield 370 attached to a back side 314 of the implant. The coating or shield is discussed further in reference to FIGS. 19A-20C, below.

Figure 11:
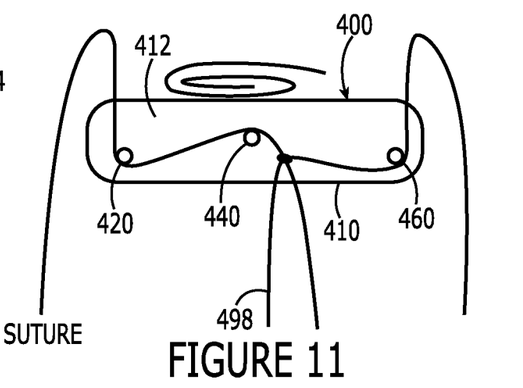
FIG. 11 is a top-view illustration of an implantable medical device including suture engaging members in the form of multiple posts for engaging a suture with the device in accordance with further aspects of an exemplary embodiment of the invention.

The dimensional and angular configurations given to each of the posts, cleats, and/or hooks may vary without departing from the scope and spirit of the current invention. In exemplary embodiments, the posts 220, 240, 320 and 340 are given a generally L-shaped configuration opening towards the left and right sides of the implant housing and connecting to the top side of the implant housing. It is contemplated that the post(s), cleat(s) and/or hook(s) may be constructed of two or more component features that are operationally connected to one another. It is further contemplated that the dimensional characteristics of the arm may be varied to accommodate differently sized implantable devices and/or suture sizes.

With particular reference to FIG. 9, a cleat 220 may be configured with a secondary retention feature. More particularly, a free end of cleat 220 (opposite the end connected to the top side 212 of housing 210) may be configured to present a reduced slot through which the suture may be introduced to the cleat 220. The reduced slot may also act as a stop to assist in preventing the suture from coming out of the cleat 220.

It is contemplated that these cleat, post, or hook features may be integrally formed or inter-connectable with the housing and/or header or connector assembly of the implant. In the case of a plastic header or body, they could be molded or machined in, or added on. In the case of a metal can, they could be welded on. Topologically, they are similar to the portions of the implant outside the slotted suture holes shown in FIGS. 8A and 8B.

As shown in FIGS. 10 and 11, these features need not occupy the full thickness of the implant, nor need they necessarily be positioned to lie on its equator. An implant 400, shown in FIG. 11, includes a first post 420, second post 440 and third post 460 connected to a top side 412 of the housing 410 of the implant and horizontally offset so that they do no lie in a straight line on top of the housing. This exemplifies that the posts may be moved towards the end(s) (outer edge of the implant housing) of the top side 412, toward the skin surface, to facilitate engagement by a suture pulling the implant inward, while adding post 440 in the middle in a deeper plane, to engage the same suture and pull the knotted segment inward, to hold the bulky knot away from the surface of the skin. This avoids a palpable bump which may predispose to wound erosion or breakdown and may promote the addition of some tension into the suture which may further assist in preventing movement or flip-over of the implant within the pocket.

The features contemplated are schematically shown as posts, cleats, clips, and similar protrusions from the surface of the implant. They are presented as alternative suture engaging members to holes and slots within the contour of the implant, but these are not mutually exclusive, and they may be used in combination. For example a post to retain the suture knot might be added to the slotted design shown in FIGS. 8A and 8B, or a groove or recess might be molded or machined into the header to perform the same function.

It is contemplated that the number of suture engagement or retention features may vary from one to greater than three. The positioning of these features may also vary from the exemplary embodiments illustrated, such that regardless of the numeric configuration, they provide at least one or more of the functional capabilities described above. For instance, the three cleat configurations shown in FIG. 11 (or any other configurations) may promote an increase in the tangential nature of incident forces acting upon the implant and the suture when in operation thereby decreasing unwanted strain.

Figure 12:
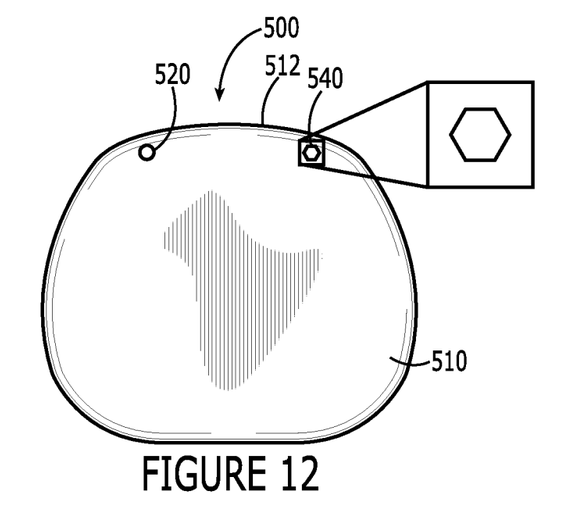
FIG. 12 is an illustration of an implantable medical device including suture holes configured as keyholes in accordance with further aspects of an exemplary embodiment of the invention.

Suture channels 124 and 144 in an implant may optionally serve as a "keyhole" so as to prevent rotation of a device, such as an implant retaining appliance, inserted within the hole. For instance, a shaft, post or pin of an implant retaining appliance may be configured in a complimentary manner to that of the keyhole. Thus, it is contemplated that an implant retaining appliance (described in detail below) can function as the matching "key" for the "keyhole". In a preferred embodiment, and as shown in FIG. 12, an implant 500 includes a housing 510 having a first suture hole 520 and a second suture hole 540 disposed therein proximal to a top side 512 of the housing 510. These suture holes are similar to that described above for FIGS. 8A and 8B, in that they provide an opening to a first and second channel that extends through the housing and terminates in a second opening, respectively. These first and second suture holes preferably provide a "keyhole" that has a hexagonal, six-sided configuration. In alternative embodiments, the keyhole may be configured in various polygonal shapes, such as square, rectangle, triangle, and others, and may include different numbers of sides, such as three-, four-, five-, seven- or more sided configurations.

Figure 13:
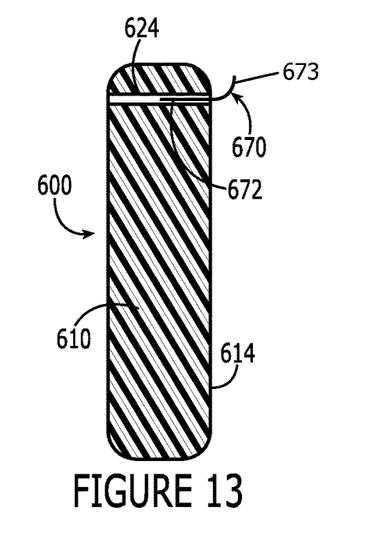
FIG. 13 is a side, cross-sectional view of the implantable medical device of FIG. 12 along section line A-A thereof and including a retaining appliance in accordance with further aspects of an exemplary embodiment of the invention.

An implant 600 of the current invention, shown in FIG. 13, includes an implant retaining appliance 670 (i.e., a hook or barb) positioned within a suture channel 624 extending through implant 600. The implant retaining appliance 670 includes a shaft 672 that is inserted, at least some partial distance, into the suture channel 624. A second end of retaining appliance 670 extends from suture channel 624 some distance away from a back side 614 of implant 600. As shown in FIG. 13, the implant retaining appliance 670 is configured as a tissue engaging hook that emerges from a back side of the implant. The particular dimensions of retaining appliance 670 may be modified to suit a particularly desired purpose as will be evident to those of ordinary skill in the art. For instance, the length of the shaft and/or an end or terminus of the implant retaining appliance may be varied.

Figure 14A:
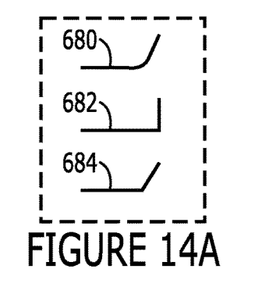
FIGS. 14A, 14B and 14C are illustrations of various retaining appliances in accordance with further aspects of an exemplary embodiment of the invention.

As shown in FIG. 14A, the implant retaining appliance(s) 680, 682 and 684 may be provided in various sizes and shapes as may be contemplated by those skilled in the art. The implant retaining appliance(s), particularly those configured as a hook, need not be particularly sharp, but are configured to provide for the secure positioning of the implant within the pocket. Thus, it is contemplated that the retaining appliance(s) may have varying thicknesses and their free ends may vary in the acuteness of the angle established. It is further contemplated that the angular orientation of the free end of a retaining appliance(s), such as the point of the hook(s), relative to a shaft of the retaining appliance may vary to provide the particular functional capabilities desired. The free end also provides a plane of engagement for the implant with the surrounding tissue of a subcutaneous pocket. This plane of engagement may be singular, consistent across multiple hooks, or varied between different hooks as will be discussed below.

Figure 14B:
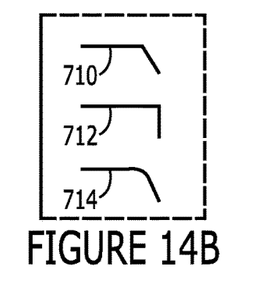
Figures 14C, 15:
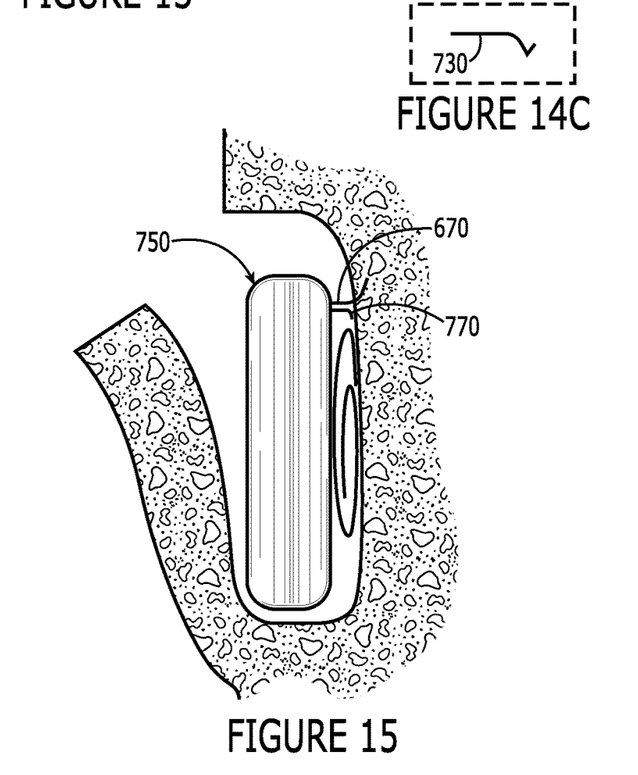
FIG. 15 is an illustration of an implantable medical device including a multi-function retaining appliance and positioned within a subcutaneous pocket.

The hook(s) promote the secure positioning of the implant in the back of the pocket by engaging with the skin or tissue surrounding the implant within the pocket as shown in FIG. 15. Once the implant is inserted in the pocket and an implant retaining appliance engages the surrounding tissue, it becomes significantly more difficult for the implant to back out of the pocket and/or flip-over.

Multiple implant retaining appliances that promote the secure positioning of an implant within a pocket may be coupled with various implantable medical devices. For instance, one hook structure may be inserted into a first suture channel and a second hook structure may be inserted into a second suture channel.

The implant retaining appliances may include a connector mechanism for securing multiple implant retaining appliances to the implant. The connector mechanism may enable the retaining appliances to be connected to the implant through the suture holes. For example, the connector mechanism may be posts or pins capable of insertion through the suture holes into the channels, wherein the posts extend at least part of the way into the channel providing a friction-fit connection. Various connection technologies, such as snap-fit, compression locking and others may be used by the current invention.

The implant retaining appliances may be integrally formed and/or inter-connectable with the implant. As indicated above, the retaining appliances can plug into the back of the implant, allowing different versions to be interchanged, and allowing them to be unplugged in the event of removal. The retaining appliances may be constructed of absorbable material, e.g. polyglycolate, intended to disappear after wound healing has occurred; or they can be non-absorbable and intended to remain.

Implants often include leads which extend from them and these leads must be effectively handled in conjunction with the proper anchoring of the implant in its desired position within a pocket.

As shown in FIG. 14B, retaining appliances may be configured as various lead retainers 710, 712 and 714 to promote lead retention in a desired position relative to the implant. Just as hooks curving upward can serve to hold the implant down in the pocket, retaining appliances configured as one or more lead retainer(s) curving downward or toward the bottom side of an implant can serve to hold the lead loop(s) or coil(s) down, beneath the implant and/or the suture holes of an implant and out of the surgical field. It is contemplated that the lead retainer configuration may vary, such as the numerous possible shapes that are shown in FIG. 14B, but that any configuration which allows the implant to operate in a desired manner and serve the function of retaining the lead loop(s) or coil(s) are contemplated to fall within the scope of the current invention.

The configuration of the lead retainer(s) may vary, both in dimension and angular orientation, such that the length, width, thickness or other dimensional characteristics, and the angle orientation of the shaft relative to a free end, and the acuteness of the angle provided at the free end, may vary without departing from the spirit and scope of the invention.

The lead retainers may be integrally formed and/or inter-connectable with the implant. The lead retainers can "plug" into the suture holes or keyholes in a manner similar to that accomplished by the hooks. In alternative embodiments, shown in FIGS. 16A-16C and 17A-17B, the lead retainers may be single, stand-alone devices or be part of a device that connects the lead retainers with various other features. For instance, the lead retainers may be a part of a lead retainer securing device that provides a connector mechanism for securing the lead retainers to the implant. The connector mechanism may enable the lead retainer securing device to be connected to the implant through the suture holes. For example, the connector mechanism may be posts capable of insertion through the suture holes into the channels, wherein the posts extend at least part of the way into the channel providing a friction-fit connection. Various connection technologies, such as snap-fit, compression locking and others may be used by the current invention.

Shown in FIG. 14C is a retaining appliance 730 including a lead retainer curving downward and an implant securing hook pointing upward, providing a single retaining appliance with a combination of the two functions. In preferred exemplary embodiments, as shown in FIG. 15, an implant 750 includes upward-curving tissue engaging hooks 760 extending in length or protruding further from the back side of the implant, so as to promote their engagement with tissue behind the pocket, than the downward-curving lead retainer 770. The working length or emergence of the lead retainer is preferably within the depth of the pocket.

Referring again to FIGS. 16A-16C, implant 800 includes an implant retaining appliance 900. Implant retaining appliance 900 includes a lead retainer 910 integrally connected with tissue engaging hooks 940, 950 and 960. The hooks are similar to those described and shown in FIGS. 13 and 14A. Alternative configurations for the hooks of the implant retaining appliance 900 may be used. The multiple tissue engaging hooks are generally configured as independent hooks positioned with respect to one another to provide a similar plane for their engagement with tissue once the implant is positioned within a pocket. The plane of engagement for the hooks is preferably consistent among and between the different individual hooks. It is contemplated that the various independent hooks may establish separate, independent engagement planes. For instance, the extent to which each of the hooks emerges from implant 800 may be configured differently, thereby establishing different engagement planes for each.

The implant retaining appliance 900 may include a connector mechanism for securing the retaining appliance to the implant. The connector mechanism may enable the retaining appliance to be connected to the implant through the suture holes. For example, the connector mechanism may comprise posts or pins capable of insertion through the suture holes into the channels, wherein the posts extend at least part of the way into the channel providing a friction-fit connection. Various connection technologies, such as snap-fit, compression locking and others may be used by the current invention.

The tissue engaging hooks may be integrally formed and/or inter-connectable with the implant. As indicated above, the tissue engaging hooks and/or lead retainers in combination with the connector mechanism can plug into the back of the implant, allowing different versions to be interchanged, and allowing them to be unplugged in the event of removal. The various component features of the retaining appliances may be constructed of absorbable material, e.g. polyglycolate, intended to disappear after wound healing has occurred; or they can be non-absorbable and intended to remain.

Figures 16A, 16B, 16C:
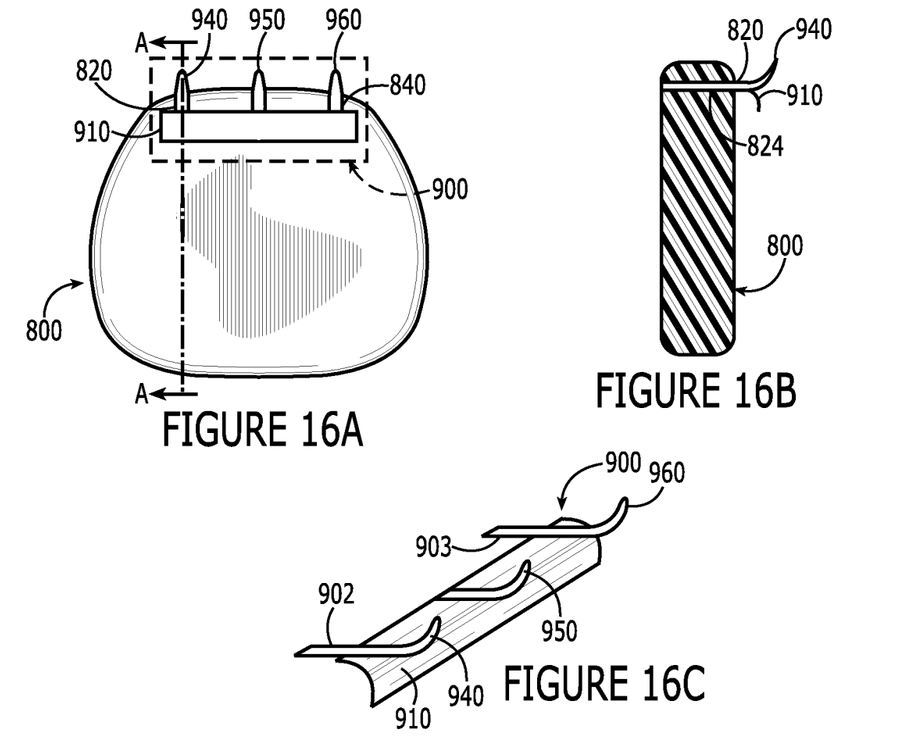
FIG. 16A is an illustration of an implantable medical device with a multi-function retaining appliance attached thereto.
FIG. 16B is a side, cross-sectional view of the implantable medical device of FIG. 16A along Section line A-A.
FIG. 16C is a perspective view of the multi-function retaining appliance of FIGS. 16A and 16B.

In a preferred embodiment, the implant retaining appliance 900, as shown in FIGS. 16A-16C, includes a first connector pin 902 and a second connector pin 903. The first and second connector pins are configured to insert within first suture hole 820 and second suture hole 840, respectively, of the implant 800. The first and second connector pins provide for the secure connection between the implant 800 and implant retaining appliance 900. This double-pin configuration stabilizes the assembly against rotation. The configuration of connector pins 902 and 903 may vary, such as by providing such connector pins in a "key-shape" to engage with a "keyhole" configuration of the suture holes. As best seen in FIG. 16C, lead retainer 910 comprises a curved surface extending generally outward and downward from channel 824 and extends across the face of implant 800.

In the embodiment shown in FIGS. 16A-16C, the lead retainer feature is generally configured as a continuous, partially cylindrical, elongate surface that forms a continuous edge along the width of the implant. It is contemplated that the configuration of the lead retainer(s) may vary from the generally partially cylindrical shape and/or be non-continuous.

Figure 17A:
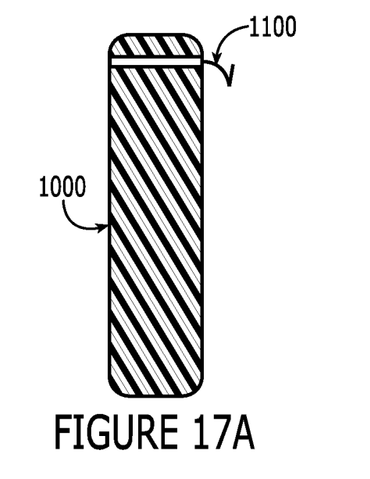
FIG. 17A is a side, cross-sectional view of an implantable medical device with a multi-function retaining appliance attached thereto.
Figure 17B:
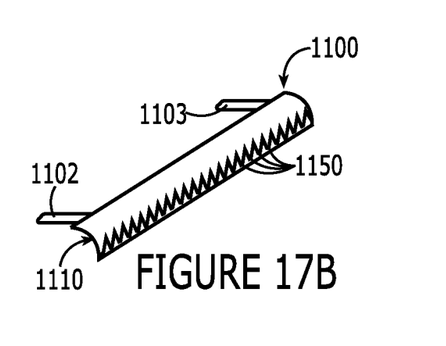
FIG. 17B is a perspective view of the multi-function retaining appliance of FIG. 17A.

In an alternative embodiment, as shown in FIGS. 17A-17B, implant 1000 is similar to implant 800, but includes a retaining appliance 1100 connected to the implant through the use of pins 1102 and 1103 in a manner similar to that described for retaining appliance 900. The lead retainer 1110 is similar to the lead retainer 910 described above except in the manner in which the tissue engaging hooks 1150 are connected proximal to a bottom edge of the lead retainer 1110. Also, the hooks may optionally be configured as multiple tiny hooks 1150, similar in configuration to hook-and-loop fastening material, such as Velcro®.

Coils of redundant lead and catheter can be unwieldy during implantation, especially if there is a considerable length of redundancy and/or multiplicity of leads or catheters, and thus multiple coils. Absorbable sutures can be tied around the coils to retain them, but this is cumbersome, requiring a modicum of surgical skill, and even assuming such skill it is best done by two people.

Figure 18A:
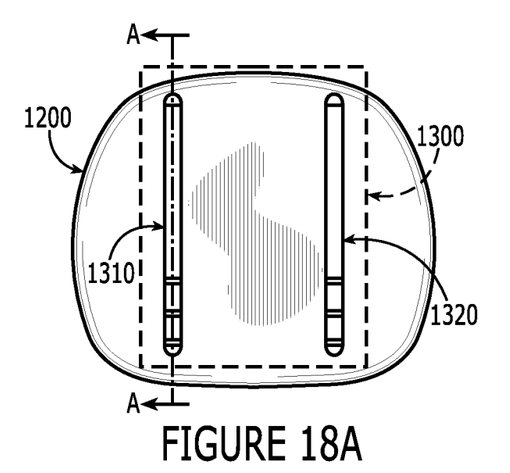
FIGS. 18A through 18C illustrate an implantable medical device having a retaining appliance attached thereto in the form of a clip for retention of lead coils.
Figure 18B:
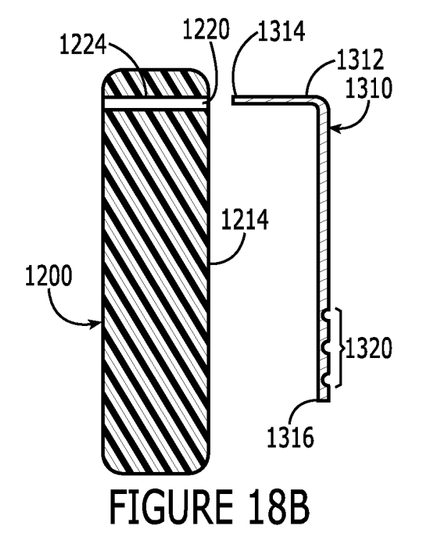
Figure 18C:
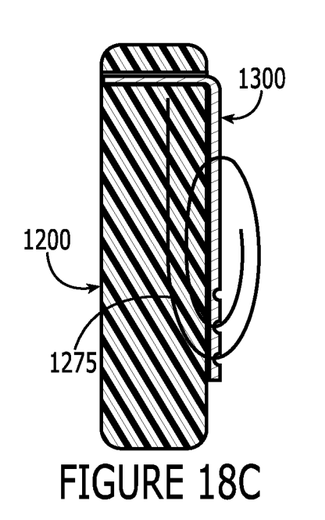

As shown in FIGS. 18A-18C, the retaining appliance may comprise a clip assembly 1300 connected to an implant 1200 into which the redundant lead may be inserted so as to retain the lead. Such assembly can be managed by one person, and thus promotes the effective management of one or more coils which sometimes complicate implantation.

The clip assembly 1300 preferably includes a first clip 1310 and a second clip 1320. The first and second clips are similar, such that the description provided below regarding the first clip 1310 should be understood to be applicable to the second clip 1320. Both the first and second clips may be constructed of bio-absorbable material (e.g., polyglyconate) so as to provide retention during surgery and then, after several weeks, disappear so that the redundant lead is mobile and can provide strain relief.

Clip 1310 includes a shaft 1312, the configuration of which may vary, both in dimension and angular orientation, such that the length, width, thickness or other dimensional characteristics, and the angle orientation of the shaft relative to an implant or either the implant connector or lead connector, may vary without departing from the scope and spirit of the instant invention. It is further contemplated that the dimensional characteristics of the shaft may vary to accommodate implant devices of varying characteristics.

A first end 1314 of clip 1310 can be used to couple the clip 1310 with an implant. First end 1314 may include an implant connector mechanism to accomplish the purpose of securely affixing the position of the clip 1310 relative to the implant. A second end 1316 of clip 1310 includes a lead connector mechanism 1320 configured to receive and secure the position of a lead coil 1275.

The first end 1314 of clip 1310 may be configured as a post or pin that is capable of connecting with a suture hole, such as suture hole 1220 and suture channel 1224 in the implant 1200, but in the field the operator may wish to cut the post away and use the clip(s) in a free-floating manner or freestanding fashion. The first end 1314 may be integrally formed or inter-connectable with the rest of the shaft 1312 and/or lead connector mechanism 1320 of the clip 1310.

As shown in the exemplary embodiments of FIGS. 18A-18C, the clips can engage suture holes in the implant 1200 in a similar manner as that described above for the implant lead retainers discussed above. In operation, and as particularly shown in FIG. 18C, the first end 1314 of the clip 1310 is inserted into suture hole 1220. The insertion allows the shaft and lead connector mechanism to be positioned in a generally flush manner relative to a back side 1214 of the implant. The lead or coil 1275 may then engage the notches or clips of the lead connector mechanism 1320, thereby accomplishing the positioning of the coil proximal to the side of the implant. The positioning of the coil by the clip also promotes the use of sutures to secure the position of the implant within a pocket.

In the current embodiment, the implant 1200 is engaged by a first clip 1310 and second clip 1320 in an inter-connectable manner. Alternatively, the clip may be integrally formed with the implant. The configuration of the implant connector mechanism may vary, both in dimension and angular orientation, such that the length, width, thickness or other dimensional characteristics, and the angle orientation of the implant connector mechanism relative to an implant or either the shaft or lead connector, may vary without departing from the scope and spirit of the instant invention.

The first end 1314 of clip 1310 may also include various other features. For example, a tissue engaging hook and/or a lead retainer as discussed above may be included. These features can be integrated into or inter-connectable with the shaft 1312 of the clip 1310.

The second end 1316 includes the lead connector mechanism 1320 of the clip 1310 and is integrally formed as part of shaft 1312. The lead connector mechanism 1320 is configured to provide for the retention of the lead loop(s) or coil(s) in a position relative to the implant that promotes the efficient insertion, placement and securing of the position of the implant in the pocket. The configuration of the lead connector mechanism may vary, both in dimension and angular orientation, such that the length, width, thickness or other dimensional characteristics, and the angle orientation of the lead connector mechanism relative to an implant or either the shaft or implant connector, may vary without departing from the scope and spirit of the instant invention. It is contemplated that the lead connector mechanism may be inter-connectable with the shaft 1312 of the clip 1310 allowing a user to interchange various different lead connector(s) with various shafts.

In the current exemplary embodiments, the lead connector mechanism 1320 includes multiple notches or clips disposed along the second end 1316 of the shaft 1312, and the spatial relation among these notches or clips allows each to engage a lead to promote its secure positioning relative to the implant. The lead connector mechanism may include more or less than the connectors shown. Further, the connectors may be variously positioned along the length of the shaft 1312 to accomplish their function. It is further contemplated that one or more of the connectors may be a "hole" through which the lead(s) may be inserted to allow a user to place the lead in a desired position. The configuration of the notches or clips of the lead connector mechanism 1320 may vary and numerous technologies may be employed, such as a compression lock mechanism, friction-fit mechanism, snap-fit mechanism, and others as may be contemplated by those skilled in the art.

Figure 19A:
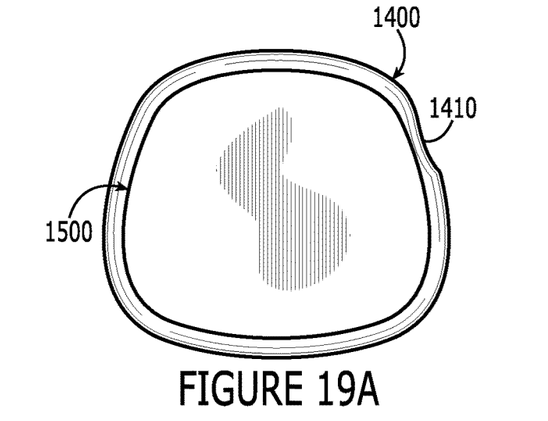
FIGS. 19A and 19B illustrate a coating or shield used with an implantable medical device in accordance with further aspects of an exemplary embodiment of the invention.
Figure 19B:
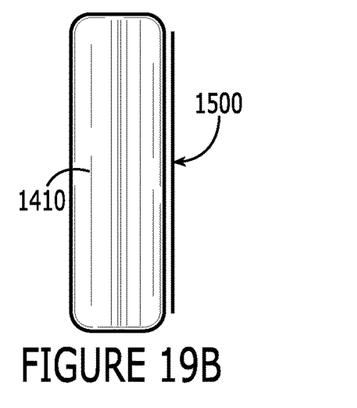

Additionally, lead retaining devices may be provided that may couple with an implantable medical device that also provide a protective function for the implant and/or the lead or lead coils extending from the implant. For example, as shown in FIGS. 19A and 19B, a coating 1500 may be applied to housing 1410 of an implant 1400. The coating 1500 is preferably a sirolimus or a similar compound to inhibit scar formation. The redundant loops or coils of lead behind the implant serve an important function in providing strain relief, and scar tissue enveloping them may compromise this. Coating the back of the implant may help preserve this function. It is further contemplated that coating the proximal lead segment may likewise provide a similar functional benefit.

Figures 20A, 20B:
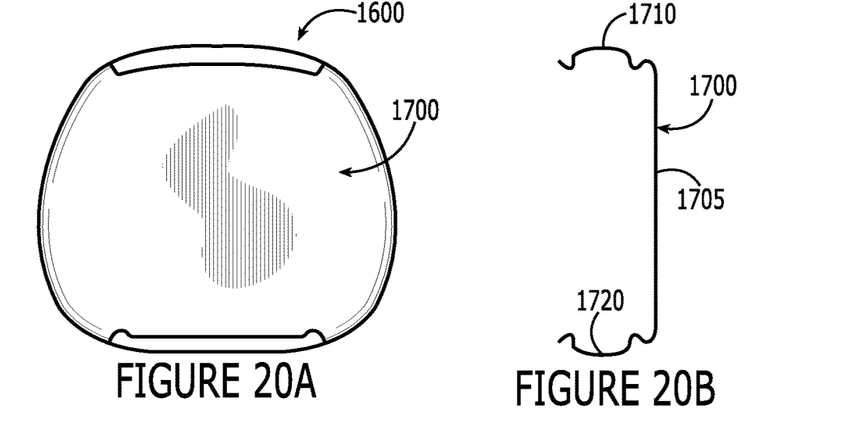
FIGS. 20A, 20B and 20C illustrate a ferrule used with an implantable medical device in accordance with further aspects of an exemplary embodiment of the invention.
Figure 20C:
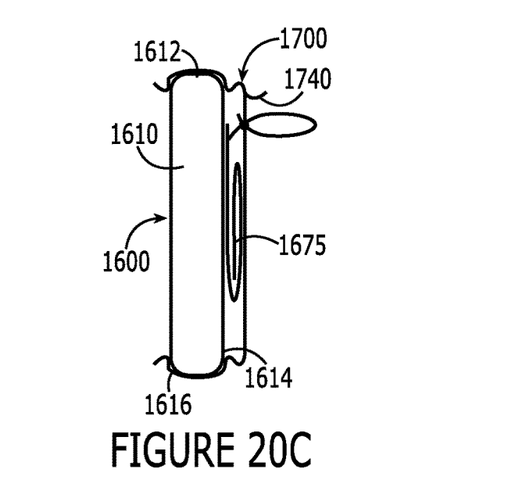

As shown in FIGS. 20A-20C, the lead retaining device may also include a separate ferrule, cap or shield 1700 positioned on implant 1600. Shield 1700 is interposed between the implant 1600 and the tissues behind it when the implant is positioned within the subcutaneous pocket. In operation, the coils of lead 1675 lie between a back side 1614 of a housing 1610 of the implant 1600 and a back plate 1705 of shield 1700. Optionally, the coils of lead may lie behind the shield or between two shields. The shield may serve to provide strain relief and inhibit the development of scar tissue about the coiled lead and/or proximal lead segment. The space between the clip and the back of the implant may accommodate the coils of the lead so that they remain un-encapsulated in scar tissue and thus free to glide and provide strain relief. The shield may be constructed of various materials, such as Teflon or other such non-adhering, biologically inert material as may be contemplated by those skilled in the art.

The shield 1700 may be mechanically coupled to the implant 1600, as shown in FIG. 20C, utilizing a snap-fit connection for securely connecting with and affixing the position of the shield relative to the implant. The shield 1700 could be contoured into a ferrule, fairing or clip that extends a shield top 1710 around a top side 1612 of the implant housing 1610 and a shield bottom 1720 around a bottom side 1616 of the implant housing 1610, so that the shield 1700 clips into place (like a cell phone or beeper in a belt clip). Other connection technologies, such as a friction-fit or various other mechanisms may be employed. In the alternative, the shield 1700 may be free floating.

The shield 1700 is preferably configured to cover the entire surface of the back side 1614 of the housing 1610 of the implant 1600. Alternatively, the shield may cover only a portion of the implant 1600. The shield may be continuous (solid), as shown, or fenestrated.

The shield 1700 may also include an implant securing device 1740 connected to and extending from shield plate 1705 proximal to the shield top 1710, as shown in FIG. 20C. The implant securing device may be configured in a manner similar to that described previously and shown in FIGS. 13-17, or may be alternatively configured as contemplated by those skilled in the art.

It is believed that the present invention and many of its attendant advantages will be understood by the forgoing description. It is also believed that it will be apparent that various changes may be made in the form, construction and arrangement of the components thereof without departing from the spirit and scope of the invention or without sacrificing all of its material advantages. The form herein before described is merely an explanatory embodiment thereof.

INDUSTRIAL APPLICABILITY

The present invention is applicable to surgical medical devices and related methods. The invention discloses an implantable medical device and related method configured for securely attaching the device to tissues in a patient's body while minimizing the manual dexterity required to accomplish such attachment. The device can be made in industry and practiced in the medical field.

I claim:
1. An implantable medical device comprising:
an implantable medical device housing forming an exterior of either an implantable electrical stimulation device or an implantable drug delivery device, said housing having a front, flat planar face, a back, flat planar face, an edge face extending around a perimeter of said housing between the front planar face and the back planar face, and at least one catheter connection; and
a plurality of suture engaging members each configured to receive a portion of a single suture therein, wherein said suture engaging members are positioned on said housing with respect to one another such that tightening a single suture that simultaneously engages both of said suture engaging members and extends through tissue within a patient's body against which said housing is to be implanted will cause said housing to be pulled against said tissue.

2. The implantable medical device of claim 1, further comprising a first suture channel extending through said housing from said front face of said housing to said back face of said housing, and a second suture channel extending through said housing from said front face of said housing to said back face of said housing, wherein each of said suture engaging members further comprises a slot extending from an outer edge of said housing into one of said first suture channel and said second suture channel.

3. The implantable medical device of claim 1, wherein each of said suture engaging members further comprises a fastening post positioned on an upper surface of said edge face of said housing.

4. The implantable medical device of claim 3, wherein each of said fastening posts further comprises a first generally L-shaped hook opening toward a first side of said housing and a second generally L-shaped hook opening toward a second side of said housing opposite said first side.

5. The implantable medical device of claim 3, further comprising at least three fastening posts extending upward from said upper surface of said edge face of said housing, wherein at least one of said fastening posts is horizontally offset from at least one other fastening posts so that said fastening posts are not situated in a straight line on said upper surface of said housing.

6. The implantable medical device of claim 1, further comprising:
at least one channel extending into said housing; and
a retaining appliance removably positioned within said channel, said retaining appliance having a connecting arm configured to fit within and remain removably held within said at least one channel, and a retaining arm attached to said connecting arm and extending away from said connecting arm at an angle to said connecting arm.

7. A method for securing the position of an implantable medical device, comprising:
providing an implantable medical device, said implantable medical device further comprising an implantable medical device housing forming an exterior of either an implantable electrical stimulation device or an implantable drug delivery device, said housing having a front, flat planar face, a back, flat planar face, an edge face extending around a perimeter of said housing between the front planar face and the back planar face, and at least one catheter connection, and a plurality of suture engaging members each configured to receive a portion of a single suture therein, wherein said suture engaging members are positioned on said housing with respect to one another such that tightening a single suture that simultaneously engages both of said suture engaging members and extends through tissue within a patient's body against which said housing is to be implanted will cause said housing to be pulled against said tissue;

forming a subcutaneous pocket in a patient's body having an interior pocket wall;

placing a suture through said back wall of said pocket;

removing a sewing needle from said suture so as to provide two free ends of said suture;

tying said free ends of said suture to cause said suture to form a tightenable suture loop;

inserting portions of said tightenable suture loop into said suture engaging members; and tightening said suture loop so as to draw said implantable medical device into a final implanted position within said pocket.

8. The method of claim 7, wherein said implantable medical device further comprises at least one channel extending into said housing, and a retaining appliance removably positioned within said channel, said retaining appliance having a connecting arm configured to fit within and remain removably held within said at least one channel, and a retaining arm attached to said connecting arm and extending away from said connecting arm at an angle to said connecting arm, further comprising the steps of:

upon tightening said suture loop, causing at least a portion of said retaining arm to penetrate subcutaneous tissue on said back wall of said pocket so as to anchor said housing to said back wall.

9. The method of claim 8, wherein said implantable medical device further comprises a catheter removably connected to said housing, further comprising the steps of:

forming at least a portion of said catheter into a coil; and prior to said tightening step, positioning said coil between said housing and said back wall of said pocket and beneath at least a portion of said retaining arm.

\* \* \* \* \*